United States Patent
Bouchard et al.

[19]

[11] Patent Number: 5,876,389
[45] Date of Patent: Mar. 2, 1999

[54] SANITARY NAPKINS AND METHOD FOR COLLECTING SAMPLES OF BODILY SUBSTANCES

[75] Inventors: Céline Bouchard, Sillery; Carol Morin, Québec; Michel Fortier, Sillery, all of Canada

[73] Assignee: Ezy-Detek (EDI) Inc., Sillery, Canada

[21] Appl. No.: 668,894

[22] Filed: Jun. 24, 1996

[51] Int. Cl.⁶ .............................. A61F 13/15; A61B 5/00
[52] U.S. Cl. ..................... 604/385.1; 600/574; 600/573; 604/358
[58] Field of Search .................. 604/361, 362, 604/385.1, 358; 128/711, 638; 600/584, 574, 573

[56] References Cited

U.S. PATENT DOCUMENTS

| | | |
|---|---|---|
| Re. 24,666 | 7/1959 | Draghi . |
| 2,929,379 | 3/1960 | Poulsen .................................. 604/372 |
| 3,731,685 | 5/1973 | Eidos ...................................... 604/361 |
| 3,850,160 | 11/1974 | Denson . |
| 3,918,433 | 11/1975 | Fuisz . |
| 3,934,575 | 1/1976 | Bucalo .................................. 600/584 |
| 4,072,150 | 2/1978 | Glassman .............................. 604/378 |
| 4,114,621 | 9/1978 | Mims ..................................... 128/638 |
| 4,444,193 | 4/1984 | Fogt et al. . |
| 4,605,404 | 8/1986 | Sneider . |
| 4,789,629 | 12/1988 | Baker et al. . |
| 4,806,408 | 2/1989 | Pierre et al. ........................... 604/378 |
| 4,808,379 | 2/1989 | Wardlaw et al. . |
| 5,088,502 | 2/1992 | Miller . |
| 5,119,828 | 6/1992 | Miller . |
| 5,231,992 | 8/1993 | Leon . |
| 5,429,631 | 7/1995 | Grenier ................................. 604/378 |
| 5,432,097 | 7/1995 | Yourno . |
| 5,676,144 | 10/1997 | Schoendorfer ........................ 600/584 |

FOREIGN PATENT DOCUMENTS

| | | |
|---|---|---|
| 2 399 231 | 8/1978 | France . |
| 2 599 500 | 6/1986 | France . |
| 3810473 | 10/1989 | Germany .............................. 604/361 |
| 520576 | 4/1940 | United Kingdom ................ 604/385.1 |
| 9119471 | 12/1991 | WIPO .................................. 604/361 |
| 4010958 | 5/1994 | WIPO .................................. 604/361 |

OTHER PUBLICATIONS

Translation of DT 3810475.

*Primary Examiner*—Mark O. Polutta
*Attorney, Agent, or Firm*—Calfee, Halter & Griswold LLP

[57] ABSTRACT

A collection device for enabling the patient to self-collect substances from the body, such as fluids, secretions, cells, and infectious and non-infectious agents, takes the form in the case of substances from the genital, anal or urinary regions of a sanitary napkin used in a conventional manner in an undergarment and which comprises a porous outer sleeve open ended at one longitudinal end thereof and including upper and lower sheets. An outer surface of the lower sheet is provided with an impermeable sheet coated with an adhesive covered, before use of the sanitary napkin, with a removable protective peel-off strip. The sanitary napkin also comprises between the upper and lower sheet an absorbent layer and a removable sampling strip or filter, the latter being slidably received in the outer sleeve and extending between the upper sheet and the absorbent layer and protruding from the open end of the sleeve for removal from the sanitary napkin once bodily substances have collected thereon. The sampling strip is then typically sealingly packaged and stored until its analysis. The sampling strip can also be made more or less integral with the sanitary napkin such that the complete napkin is forwarded by the end user to the laboratory. The present invention is also concerned with methods that allow the patient to self-collect bodily substances for subsequent analysis thereof.

10 Claims, 1 Drawing Sheet

U.S. Patent   Mar. 2, 1999   5,876,389
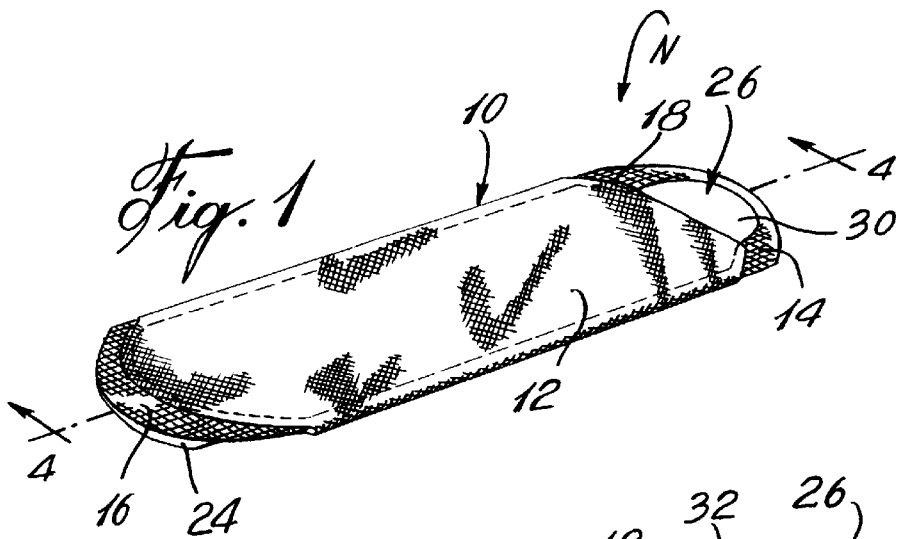
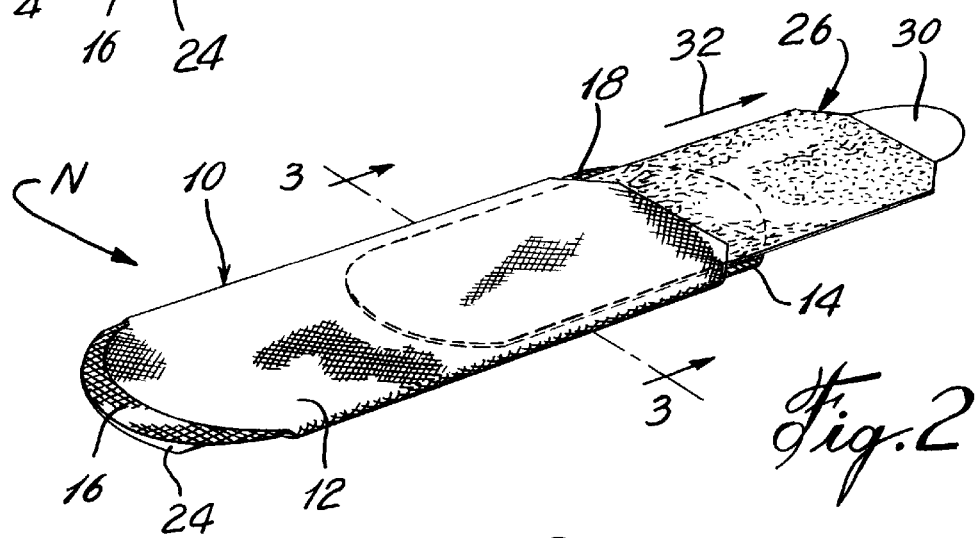
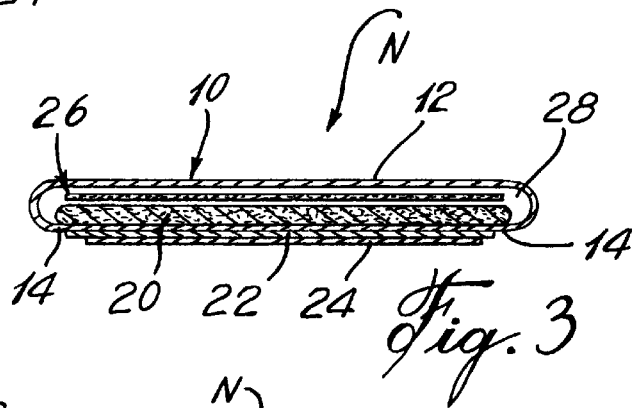
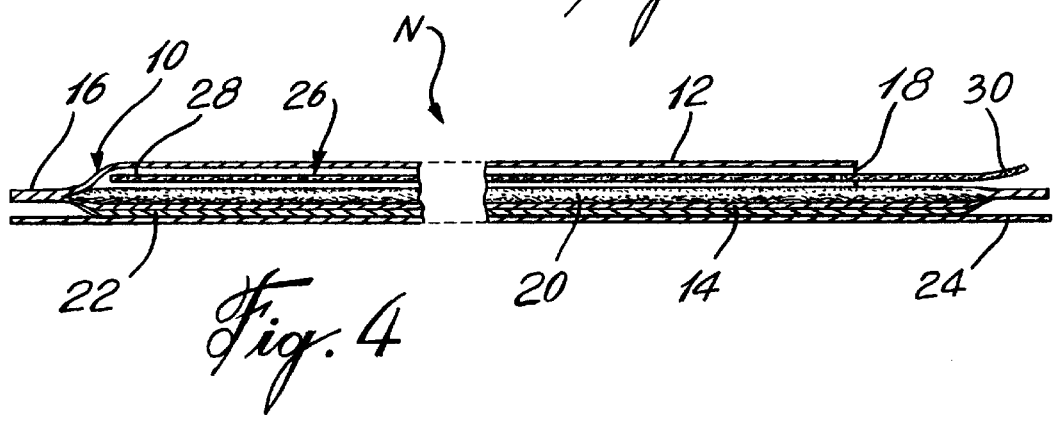

SANITARY NAPKINS AND METHOD FOR COLLECTING SAMPLES OF BODILY SUBSTANCES

BACKGROUND OF INVENTION

1. Field of the Invention

The present invention relates to collection devices for recovering samples of bodily fluids or cells for subsequent laboratory analysis and, more particularly, to a collection device and method for allowing the patient to recover samples of bodily fluids, secretions, cells, and infectious and non-infectious agents, in whole all hereinafter referred to as bodily substances, and, for instance, to a modified sanitary napkin for collecting such substances from the genital, anal or urinary regions, and to a method associated with the use thereof.

2. Description of Prior Art

U.S. Pat. No. 5,231,992 issued on Aug. 3, 1993 to Leon discloses a low-impact cervical cell and fluid collector which includes a substantially disc-shaped main body 12 which defines a generally concave recess 14 into which a porous collection membrane 16 is mounted. Therefore, when the collector 10 is in place adjacent to the patient's cervix, cells and fluids adhere to the outer surface of the membrane 16. Underneath the membrane 16, there is provided a layer 24 of a cell-moistening material or agent, such as a polymer gel adapted to release water during cell collection for moistening collected cells through the pores of the membrane 16 when the cells are adhered to the outer surface thereof. The main body 12 can be provided with a string 18 to facilitate the removal of the collector 10 from the body.

French Patent Application which was published as FR-2 599 500 on Dec. 4, 1987 in the name of Chieusse discloses a transparent adhesive strip for taking a sample directly from the skin's surface for microscopic examination or analysis, the adhesive strip comprising a rigid transparent resin or glass plate 1 covered successively with a transparent layer 2 which is self-adhesive on both of its sides, an isolating film or coating 4 of shorter length, and a semi-rigid cover layer 3 made, for instance, of strong paper or cardboard. The limited length of the film 4 defines a section 5 where the cover layer 3 adheres directly to the adhesive 2 and forms a joint line 6 which allows for the cover layer 3 to be pivotally lifted about the hinge 6, wherein in a closed position 7, the sample-taking surface 9 is protected for its transport or storage, whereas in its open position 8, the adhesive surface 2 can be brought into direct contact with the skin's surface such as to enable the adhesive strip 2 to remove and collect desired samples from the skin and other surfaces for subsequent analysis thereof.

U.S. Re-Issue Pat. No. RE 24,666 issued on Jul. 7, 1959 to Draghi discloses a tampon for the detection of cancer of the pelvic region. More particularly, the tampon of this U.S. Patent constitutes a preliminary diagnosis method which determines if there are present any indicia of cancer by taking a sample of cells which are present in the cervical canal and in the vagina and by the subsequent microscopic analysis of these cells. The tampon includes a tampon body 10 partly covered by a jacket 12 terminating with an enlarged cap 13 and, at the other end of the tampon body 10, there is provided a string 22. The assembly of the body 10 and jacket 12 forms a detection tampon 14. The enlarged cap 13 which closes one end of the tampon 14 is adapted to extend farthest into the vaginal canal and to collect and retain in moist form cells thereof. The jacket 12 also collects cells and retains them in a relatively moist condition thereby ensuring a more accurate clinical evaluation.

U.S. Pat. No. 3,850,160 issued on Nov. 26, 1974 to Denson discloses a diagnostic tampon 10 having a supporting body 13 covered by an outer film 12 and provided at one end thereof with a removal string 11. The tampon is particularly adapted for collecting cellular material from body cavities, in particular from the vaginal cavity, for subsequent examination.

U.S. Pat. No. 5,432,097 issued on Jul. 11, 1995 to Yourno teaches a method for the recovery of blood cells from dried blood spots on a filter paper.

U.S. Pat. No. 5,119,828 issued on Jun. 9, 1992 to Miller discloses a device 10 for collecting sebum which is secreted by the sebaceous glands of a patient, the device 10 including a microporous film 12 which is opaque to light when the pores are filled with gaseous material and which is substantially translucent when the film pores are filled with sebum. The film 12 is mounted to a substrate 14 which defines a light absorbing area 16 for enhancing visualization of the pores of the film 12 when filled with sebum. In use, the device is pressed against the patient's skin surface such that the film 12 contacts the skin and absorbs its sebum, whereby a sebum spot pattern is developed in the film 12 and is visually enhanced by way of the light absorbing area 16.

U.S. Pat. No. 5,088,502 issued on Feb. 18, 1992 to Miller discloses a device 10 for sampling the surface of the skin which includes a substrate 12 having a light absorbing area 14 disposed thereon with an adhesive layer 16 being disposed on the substrate 12 such as to overlie the light absorbing area 14. The adhesive layer 16 is optically clear and under pressure conforms to the surface of the skin to be sampled. A removable protective film 18 provided with a tab 20 is disposed on the adhesive layer 16 for protecting the same prior to use of the device. The device and, more particularly, the adhesive layer 16 is placed against the skin surface such that, when removed, skin cells adhere to the adhesive layer 16. The sampled cells can then be visualized in view of the light absorbing area 14.

U.S. Pat. No. 4,789,629 issued on Dec. 6, 1988 to Baker et al teaches a device for collecting and testing fecal occult blood which includes a pocket-like member 16 and an absorbent insert 24 disposed in the pocket member 16. The pocket member 16 is disposed on the inside front cover of the device such that when the cover is in a closed position thereof, the pocket 16 overlies the fecal smear on the specimen receiving sheet 36, whereby with one single collection, two separate membranes, that is the specimen receiving sheet 36 and the absorbent insert 24, receive the components of the fecal sample and can be individually and independently tested.

U.S. Pat. No. 4,808,379 issued on Feb. 28, 1989 to Wardlaw et al discloses a device for obtaining stool samples and detecting occult blood and which is used in a way similar to toilet tissue to obtain a stool sample on a receptor sheet 26 provided in the device. Therefore, to obtain the stool sample, the patient, after defecation, draws the cover sheet 32 and its holes 34 across the rectum in the same manner as toilet tissue such that stool is thus wiped onto the cover sheet and passes through the openings 34 and deposits in spots on the receptor sheet 26. The cover sheet 32 is then peeled off and discarded, thereby exposing the stool spots S of the receptor sheet 26, after which the stool spots S can be effectively sealed in the device by folding the impermeable sheet 2.

SUMMARY OF INVENTION

It is therefore an aim of the present invention to provide an improved device for allowing a patient to collect externally from the body samples of bodily substances, such as fluids, cells, tissues, microorganisms, etc.

It is also an aim of the present invention to provide an improved method for allowing a patient to collect externally from the body samples of bodily substances, such as fluids, cells, tissues, microorganisms, etc.

It is a further aim of the present invention to provide a modified sanitary napkin for collecting samples of bodily substances from the genital, anal or urinary regions and, for instance, vaginal secretions.

It is a still further aim of the present invention to provide a modified sanitary napkin provided with an absorbent layer for collecting the samples of bodily substances from the genital, anal or urinary regions.

It is a still further aim of the present invention to provide a collection device, such as a modified sanitary napkin, having a removable collection strip, membrane or filter, in particular in the form of an absorbent strip, slidably received in a pocket defined in the collection device or sanitary napkin.

Therefore, in accordance with the present invention, there is provided a collection device for collecting bodily substances from the genital, anal or urinary regions, comprising a substantially flexible and comfortable member adapted to be positioned such that a receiving surface of said member is located substantially opposite a location from which a sample of bodily substance is to be taken, collecting means in said member and in communication with said receiving surface, whereby sufficient bodily substance contacting said receiving surface is at least partly collected by said collecting means for subsequent analysis thereof.

Also in accordance with the present invention, there is provided a collection device for allowing a user to collect bodily substances, comprising a member adapted to be externally worn by the user such that a receiving surface of said member is located substantially opposite a location of the user at which a sample of bodily substance is to be taken, collecting means in said member and in communication with said receiving surface, said collecting means being removable from said member by the user, whereby once sufficient bodily substance having contacted said receiving surface has been at least partly collected by said collecting means, said collecting means is removed from said member for subsequent analysis thereof.

Further in accordance with the present invention, there is provided a method of self-collection of bodily substances, comprising the steps of:

(a) self-positioning collector means externally on a user and at a location of the user at which a sample of bodily substance is to be taken; and (b) collecting on said collector means at least one bodily substance from the user.

BRIEF DESCRIPTION OF THE DRAWINGS

Having thus generally described the nature of the invention, reference will now be made to the accompanying drawings, showing by way of illustration a preferred embodiment thereof, and in which:

FIG. 1 is a perspective view of a modified sanitary napkin in accordance with the present invention;

FIG. 2 is a perspective view of the sanitary napkin of FIG. 1 but illustrated with its removable absorbent sampling strip partly removed therefrom;

FIG. 3 is a transversal cross-sectional view taken along line 3—3 of FIG. 2; and FIG. 4 is a longitudinal cross-sectional view taken along line 4—4 of FIG. 1.

DESCRIPTION OF THE PREFERRED EMBODIMENTS

The present invention is concerned with the collection of samples of bodily substances (such as fluids, secretions, cells, microorganisms, infectious and non-infectious agents, etc.) and, more particularly, in view of some people's reticence in having these samples taken at a clinic or hospital, with a collection device and method which allow the patient to "self-collect" the samples, typically outside of any formal medical environment, which can then be properly packaged and forwarded for subsequent analysis thereof to any appropriate medical facility, e.g. laboratory.

In the present description as well as in the appended claims, the terms "substance" and "substances" are understood to include any bodily fluids, secretions, cells, microorganisms, infectious and non-infectious agents, etc., which can be externally recovered from the body.

For instance, and in accordance with the present invention, FIG. 1 illustrates a modified sanitary napkin N which is intended for collecting substances at the genital and anal regions and which includes a porous outer sleeve 10 having upper and lower sheets 12 and 14, respectively, which are joined at a first longitudinal end 16 thereof and which are open at an opposite second longitudinal end 18 of the sleeve 10. The upper and lower sheets 12 and 14 are at least partly made of a porous fabric, typically in the form of a close knit netting. Inside the sleeve 10, there is provided an absorbent layer 20, of the type well known in the art of sanitary napkins. The absorbent layer 20 is peripherally secured to the upper and lower sheets 12 and 14 of the porous sleeve 10, apart from at the second end 18 where the absorbent layer 20 is typically only secured to the lower sheet 14 such that the opening at the second end 18 is defined between the upper sheet 12 and the absorbent layer 20, as best seen in FIG. 4.

Under or outwardly of the lower sheet 14, an insulating or impermeable layer 22 acting as a liquid impervious barrier is mounted to the lower sheet 14 and is provided with an adhesive coating on a side of the impermeable layer 22 opposite its side secured to the lower sheet 14 of the sleeve 10. A removable strip 24 is detachably mounted to the adhesive coating of the impermeable layer 22 such that it can be removed therefrom when the sanitary napkin N is to be attached to an undergarment.

Intermediate the upper sheet 12 of the sleeve 10 and the absorbent layer 20, a removable absorbent sampling filter or strip 26 is slidably received in a pocket 28 which is defined between the upper sheet 12 and the absorbent layer 20 and which is open at the second end 18, again as best seen in FIG. 4. The sampling strip 26 is provided at an outside end thereof with a handling tab 30. The sampling strip 26 can be made, for instance, of a semi-porous and absorbent material, e.g. a sheet-like filter made of paper, of synthetic or non-synthetic fabrics, etc., such as to allow the patient to collect substances, for instance vaginal secretions, as samples for subsequent analysis thereof in a laboratory or the like while allowing for excess secretions and fluids to pass therethrough and reach the absorbent layer 20 and to be collected thereon.

In the present embodiment of the invention which takes the form of the sanitary napkin N, the description might refer to vaginal secretions instead of the more general "substances" mentioned hereinabove, but this is only done for illustration purposes, that is as an example of a use of the present sanitary napkin N and is obviously not intended to restrict the scope of use of any collection device in accordance with the present invention to the single collection of vaginal secretion samples.

More particularly, in use, the sanitary napkin N has the form generally shown in FIG. 1 with its removable strip 24 being removed therefrom such as to allow the sanitary napkin N to be attached to an undergarment. Subsequently, vaginal secretions, for example, will come into contact with the sanitary napkin N and, more particularly, with the upper sheet 12 of the sleeve 10 thereof. Through the netting of the upper sheet 12, the vaginal secretions will then reach the sampling strip 26, whereat some of the secretions will be absorbed and retained by the sampling strip 26 with the remainder of the secretions filtering therethrough and reaching the absorbent layer 20. Therefore, a sampling of vaginal secretions will have collected on the sampling strip 26 which, before the sanitary napkin N is discarded, is removed from the sanitary napkin N as per arrow 32 of FIG. 2, whereby the sampling strip 26 can then be properly packaged and sent, for instance, to a laboratory to be analyzed.

Therefore, the sanitary napkin N of the present invention which is intended to facilitate and render more accessible the uncovering, for example, of sexually transmitted diseases by reducing some people's resistance to showing up at clinics to be tested by way of the collection of samples for analysis purposes, is considered to meet this object as, clearly, the simple use in a typically well-known fashion of a substantially recognizable sanitary napkin N will allow for a proper sampling of bodily substances, such as vaginal secretions, to be easily obtained and forwarded to a laboratory, using the present absorbent sampling strip or filter 26 as a collection medium which is typically sealed in an appropriate container once it has been removed from the sanitary napkin N, and until it is ready to be analyzed in the laboratory.

In the laboratory, the sampling filter 26 can be analyzed by way of known techniques, such as polymerase chain reaction (PCR) and ligase chain reaction (LCR) techniques, etc.

Accordingly, the present sanitary napkin N which is based on modifications made to conventional sanitary napkins can be easily used by the patient as a collection and reception medium for various substances (e.g. secretions) provided externally of the genital, anal or urinary regions, from which a sample can then be obtained by removing the sampling strip 26 from the sanitary napkin N.

The present invention also contemplates having a non-removable, i.e. at the level of the end user, sampling filter or strip or collector installed in the sanitary napkin, whereby the complete sanitary napkin would be sent to the laboratory, whereat it would be appropriately dismantled to retrieve its sampling strip for the analysis thereof.

Furthermore, by the present invention, there is also provided a method of collecting samples of bodily substances, such as of secretions emitted at the genital, anal or urinary regions, by providing a collection medium which is adapted to be positioned at an appropriate location, for instance in the undergarment, and externally of the user, and which is further adapted to receive and/or collect samples of bodily substances, the samples being then typically properly packaged for the subsequent analysis thereof.

The present collection device, which has been herein preferably shown and described in the form of the sanitary napkin N for collecting vaginal secretions, as well as the present collection method can obviously be also used to collect various other bodily substances, such as biological fluids, blood, tissues, microorganisms or cells (again all herein generally referred to as substances), for instance, from the genito-urinary tract or system and/or from the anal region.

Accordingly, various applications of the collection device are foreseen, such as (1) for the analysis of products accumulated in the sampling filter or strip 26, including research on and identification of infectious agents (e.g. chlamydia, HIV, gonorrhea, herpes, cytomegalovirus, human papillomavirus, mycoplasma, ureaplasma, candida and other infectious and non-infectious agents, etc.) or parasites (e.g. trichomonas) or any other biochemical particle or component originating from these agents with a view of identifying and treating these agents by known techniques as well as by techniques which will be developed; (2) for the analysis of cells from the genito-urinary or intestinal system for the chromosomal, histological, cytological, biochemical or biomolecular analysis thereof; (3) for the analysis of the menstrual blood, or its derivatives (e.g. antibodies) and of any other molecule detected in the sampling strip 26; (4) for the analysis of urine, of its derivatives and of any other molecule originating from the urinary system and detected in the sampling strip 26; and (5) for the analysis of products derived from the pilosebaceous system of the genital, anal and cutaneous sphere; etc.

Basically, the invention is intended to enable the patient to recover samples of secretions, fluids, etc. emitted from the body, as well as samples of cells, fluids, etc. which are present at the cutaneous level (e.g. for the collection of substances from sores, etc., such as in the case of some types of herpetic infections which manifest on the skin) and to sealingly package the collected samples which can then be forwarded to a laboratory for the analysis thereof.

We claim:

1. A collection device for collecting bodily substances from the genital, anal or urinary regions, comprising a substantially flexible and comfortable member adapted to be positioned such that a receiving surface of said member is located substantially opposite a location from which a sample of at least one predetermined bodily substance forming part of a group of bodily substances is to be taken, a sampling filter being provided in communication with said receiving surface, said sampling filter being capable of retaining at least part of said predetermined bodily substance for subsequent analysis thereof while allowing fluids to pass therethrough, at least part of said receiving surface defining openings as a netting; said member comprising sleeve means at least partly open ended at one longitudinal end thereof, and absorbent layer means in said sleeve means, said sleeve means comprising said receiving surface, said sampling filter comprising a filtering strip removably received in said sleeve means through said one end and between said absorbent layer means and said receiving surface with said receiving surface being adapted to allow the group of bodily substances to reach said filtering strip, said sleeve means comprising upper and lower sheets, said upper sheet being at least partly comprised of said receiving surface, impermeable means being provided outwardly of said lower sheet with adhesive means being outwardly provided of said impermeable means for securing said member to an undergarment, a protective removable strip being provided outwardly on said adhesive means, wherein said filtering strip is adapted to be removed from said sleeve means by the user such that when a group of bodily substances containing the predetermined bodily substance passes through said openings of said receiving surface, the predetermined bodily substance is at least partly collected by said filtering strip, wherein once sufficient predetermined bodily substance having contacted said receiving surface has been collected by said filtering strip, said sampling filter is removed from said member for subsequent analysis thereof.

2. A collection device as defined in claim 1, wherein said filtering strip is slidably received in said sleeve and between said upper sheet and said absorbent layer means, and wherein the width of said sampling filtering is substantially the same as the width of said absorbent layer means.

3. A collection device as defined in claim 1 wherein said filtering strip is slidably received in said sleeve and between said upper sheet and said absorbent layer means, said filtering strip being provided with tab means at least partly protruding from said one end for facilitating a removal of said filtering strip from said sleeve means while not extending, when in functional position in said sleeve means, outwardly of said member.

4. A collection device comprising a member adapted to be externally worn by a user such that a receiving surface of said member is located substantially opposite a location of the user at which a sample of at least one bodily substance is to be taken, a sampling filter in said member and in communication with said receiving surface, said sampling filter being removable from said member by the user and being capable of filtering bodily substances emanating from the user's body to retain thereon at least part of said at least one bodily substances, whereby once a sufficient amount of said at least one bodily substance having contacted said receiving surface has been at least partly collected by said sampling filter, said sampling filter is removed from said member for subsequent analysis thereof, at least part of said receiving surface defining openings as a netting; said member comprising sleeve means at least partly open ended at one longitudinal end thereof, and absorbent layer means in said sleeve means, said sleeve means comprising said receiving surface, said sampling filter comprising a filtering strip removably received in said sleeve means through said one end and between said absorbent layer means and said receiving surface with said openings of said receiving surface being adapted to allow the bodily substances to reach said filtering strip, said sleeve means comprising upper and lower sheets, said upper sheet being at least partly comprised of said receiving surface, impermeable means being provided outwardly of said lower sheet with adhesive means being provided outwardly of said impermeable means for securing said member to an undergarment, a protective removable strip being provided outwardly on said adhesive means, whereby said collection device is used for collecting said at least one bodily substance from the genital, anal or urinary regions.

5. A collection device as defined in claim 4, wherein said filtering strip is slidably received in said sleeve and between said upper sheet and said absorbent layer means.

6. A collection device as defined in claim 5, wherein said filtering strip is provided with tab means at least partly protruding from said one end for facilitating a removal of said filtering strip from said sleeve means; and wherein the width of said sampling filter is substantially the same as the width of said absorbent layer means.

7. A collection device as defined in claim 5, wherein said filtering strip is provided with tab means at least partly protruding from said one end for facilitating a removal of said filtering strip from said sleeve means while not extending, when in functional position in said sleeve means, outwardly of said member.

8. A sanitary napkin for allowing a user to collect bodily substances from a genital area thereof, comprising an outer member adapted to be externally worn by the user such that a receiving surface of said outer member is located substantially opposite a location of the user at which a sample of at least one bodily substance is to be taken, an absorbent core member extending within said outer member, at least part of said receiving surface defining openings as a netting, a sampling filter located in said outer member and between said receiving surface and said absorbent core, said sampling filter being capable of filtering bodily substances received from the user's genital area and having passed through said openings to retain on said sampling filter at least part of said at least one bodily substance, whereby once a sufficient amount of said at least one bodily substance has been collected by said sampling filter, at least said sampling filter can be retained for subsequent analysis of said at least one bodily substance collected thereon, said outer member comprising sleeve means, said absorbent core being located in said sleeve means, said sleeve means comprising said receiving surface with at least part of said receiving surface defining openings for allowing said bodily substances to reach said sampling filter, said sampling filter is removably engaged in said outer member, said sleeve means comprising upper and lower sheets, said upper sheet being at least partly comprised of said receiving surface, impermeable means being provided outwardly of said lower sheet with adhesive means being, outwardly provided of said impermeable means for securing said member to an undergarment, a protective removable strip being provided outwardly on said adhesive means.

9. A sanitary napkin as defined in claim 8, wherein said sleeve means is at least partly open ended at one longitudinal end thereof, said sampling filter being provided with tab means at least partly protruding from said one end for facilitating a removal of said sampling filter from said sleeve means while not extending, when in functional position in said sleeve means, outwardly of said outer member.

10. A sanitary napkin for allowing a user to collect bodily substances from a genital area thereof, comprising an outer member adapted to be externally worn by the user such that a receiving surface of said outer member is located substantially opposite a location of the user at which a sample of at least one body substance is to be taken, an absorbent core member extending within said outer member, at least part of said receiving surface defining openings as a netting, a sampling filter located in said outer member and between said receiving surface and said absorbent core, said sampling filter being capable of filtering bodily substances received from the user's genital area and having passed through said openings to retain on said sampling filter at least part of said at least one bodily substance, whereby once a sufficient amount of said at least one bodily substance has been collected by said sampling filter, at least said sampling filter can be retained for subsequent analysis of said at least one bodily substance collected thereon, said outer member comprising sleeve means, said absorbent core being located in said sleeve means, said sleeve means comprising said receiving surface with at least part of said receiving surface defining openings for allowing said bodily substances to reach said sampling filter, said sleeve means being at least partly open ended at one longitudinal end thereof, said sampling filter being removably received in said sleeve means through said one end and between said absorbent core and said receiving surface, said sampling filter being provided with tab means at least partly protruding from said one end for facilitating a removal of said sampling filter from said sleeve means and wherein the width of said sampling filter is substantially the same as the width of said absorbent core.

\* \* \* \* \*